(12) United States Patent
Liu et al.

(10) Patent No.: US 9,834,805 B2
(45) Date of Patent: Dec. 5, 2017

(54) TWO-LAYER ANALYTE SENSOR

(71) Applicant: Verily Life Sciences LLC, Mountain View, CA (US)

(72) Inventors: Zenghe Liu, Mountain View, CA (US); Huanfen Yao, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 628 days.

(21) Appl. No.: 14/138,368

(22) Filed: Dec. 23, 2013

(65) Prior Publication Data
US 2015/0177179 A1   Jun. 25, 2015

(51) Int. Cl.
| | | |
|---|---|---|
| *G01N 27/327* | (2006.01) | |
| *B05D 3/00* | (2006.01) | |
| *C12Q 1/00* | (2006.01) | |
| *G01N 3/50* | (2006.01) | |

(52) U.S. Cl.
CPC ............... *C12Q 1/006* (2013.01); *G01N 3/50* (2013.01)

(58) Field of Classification Search
CPC ............. G01N 27/3274; G01N 27/327; G01N 27/3272; A61L 2/206; A61B 5/14532; A61B 5/14546; A61B 5/1486
See application file for complete search history.

(56) References Cited

U.S. PATENT DOCUMENTS

| | | |
|---|---|---|
| 5,795,774 A | 8/1998 | Matsumoto |
| 6,653,358 B2 | 11/2003 | Bruza |
| 7,455,874 B2 | 11/2008 | Moser |
| 8,088,595 B2 | 1/2012 | Ibey |
| 8,241,819 B2 | 8/2012 | Lowe |
| 8,385,998 B2 | 2/2013 | Zhang |
| 8,437,829 B2 | 5/2013 | Mao |

(Continued)

FOREIGN PATENT DOCUMENTS

| | | |
|---|---|---|
| EP | 0 228 259 A2 | 7/1987 |
| JP | 19860013900 | 1/1986 |

(Continued)

OTHER PUBLICATIONS

Yu et al. , Biosensors and Bioelectronics, 2008, 1278-1284.*

(Continued)

*Primary Examiner* — Gurpreet Kaur
(74) *Attorney, Agent, or Firm* — McDonnell Boehnen Hulbert & Berghoff LLP

(57) ABSTRACT

An analyte sensor and a method for making the analyte sensor are disclosed. In one aspect, the analyte sensor includes a sensing membrane having a crosslinked network with an embedded analyte sensing component. In another aspect, the analyte sensor includes a protective membrane adjacent to the surface of the sensing membrane. The protective membrane can be a crosslinked, hydrophilic copolymer having methacrylate-derived backbone chains of first methacrylate-derived units, second methacrylate-derived units and third methacrylate-derived units. The first and second methacrylate-derived units have hydrophilic side chains, and the third methacrylate-derived units in different backbone chains are connected by hydrophilic crosslinks. A method for making the analyte sensor is also disclosed.

18 Claims, 3 Drawing Sheets

(56) References Cited

U.S. PATENT DOCUMENTS

| | | |
|---|---|---|
| 2004/0106166 A1 | 6/2004 | Matsumoto |
| 2010/0051479 A1 | 3/2010 | Heller et al. |
| 2010/0175992 A1 | 7/2010 | Shah |
| 2010/0279377 A1 | 11/2010 | Shah |
| 2010/0280347 A1 | 11/2010 | Shah |
| 2011/0082356 A1 | 4/2011 | Yang et al. |
| 2011/0136929 A1* | 6/2011 | Chow ............. A61B 5/14532 521/105 |
| 2012/0160708 A1 | 6/2012 | Kohli |
| 2012/0186997 A1 | 7/2012 | Li |
| 2012/0190950 A1 | 7/2012 | Yang et al. |
| 2012/0245444 A1 | 9/2012 | Otis |
| 2012/0283538 A1 | 11/2012 | Rose et al. |
| 2013/0011460 A1 | 1/2013 | Liu |
| 2013/0203147 A1 | 1/2013 | Heller |
| 2013/0197333 A1 | 8/2013 | Petisce |
| 2013/0240374 A1 | 9/2013 | Sode |

FOREIGN PATENT DOCUMENTS

| | | |
|---|---|---|
| WO | 2014210481 A1 | 12/2014 |
| WO | 2015084570 A1 | 6/2015 |
| WO | 2015100131 A1 | 7/2015 |

OTHER PUBLICATIONS

Slaughter, Journal of Diabetes Science and Technology, 2010, 320.*

Tseng, et al., "Fabrication of implantable, enzyme-immobilized glutamate sensors for the monitoring of glutamate concentration changes in vitro and in vivo" Molecules, (Jun. 5, 2014) pp. 7341-7355, whole document.

Yan, et al., "Transparent and flexible glucose biosensor via layer-by-layer assembly of multi-wall carbon nanotubes and glucose oxidase" Electrochemistry Communications, (2007) pp. 1269-1275, vol. 9, No. 6.

International Search Report for PCT/US2104/071157, dated Mar. 27, 2015.

* cited by examiner

TWO-LAYER ANALYTE SENSOR

BACKGROUND

Unless otherwise indicated herein, the materials described in this section are not prior art to the claims in this application and are not admitted to be prior art by inclusion in this section.

The continuous or semi-continuous monitoring of physiological parameters has applications in many areas of modern medicine. Electrochemical-based sensors are believed to be particularly suitable for the monitoring and quantification of analytes (e.g., glucose) in bodily fluid samples (e.g., blood, tear film, urine or interstitial fluid samples). The use of an electrochemical-based sensor that employs an analyte sensing component, (e.g., an enzyme) in conjunction with an electrode(s) allows for the quantification of an analyte in a liquid sample by detecting the product(s) produced from the reaction of the analyte sensing component and the analyte.

SUMMARY

In one aspect, an analyte sensor is disclosed. The analyte sensor includes a sensing membrane having a crosslinked network with an embedded analyte sensing component. The cross-linked network can include one or more proteins that are crosslinked with carbon-nitrogen double bonds between the nitrogen atoms of amine groups on the proteins and carbon atoms in crosslinking groups. The sensing membrane can be adjacent to a surface of an electrode.

In another aspect, the analyte sensor includes a protective membrane adjacent to a surface of the sensing membrane. The protective membrane can be a crosslinked, hydrophilic copolymer having methacrylate-derived backbone chains of first methacrylate-derived units, second methacrylate-derived units and third methacrylate-derived units. The first and second methacrylate-derived units have hydrophilic side chains that can be the same or different, and the third methacrylate-derived units in different backbone chains are connected by hydrophilic crosslinks.

In another aspect, methods for forming the analyte sensor is disclosed. The formation of the sensing membrane can involve forming a sensing mixture of one or more proteins, a crosslinking agent, and an analyte sensing component, depositing the sensing mixture onto a surface of an electrode, and curing the deposited sensing mixture to provide a sensing membrane. The protective membrane can be formed by forming a copolymer mixture of an initiator, a first methacrylate monomer, a dimethacrylate monomer, and a second methacrylate monomer, depositing the copolymer mixture on a surface of the sensing membrane, and curing the deposited copolymer mixture. The first and second methacrylate monomers can have hydrophilic side chains suitable to provide the first and second methacrylate-derived units of the protective membrane, respectively.

These as well as other aspects, advantages, and alternatives, will become apparent to those of ordinary skill in the art by reading the following detailed description, with reference where appropriate to the accompanying drawings.

DETAILED DESCRIPTION

Figure 1:
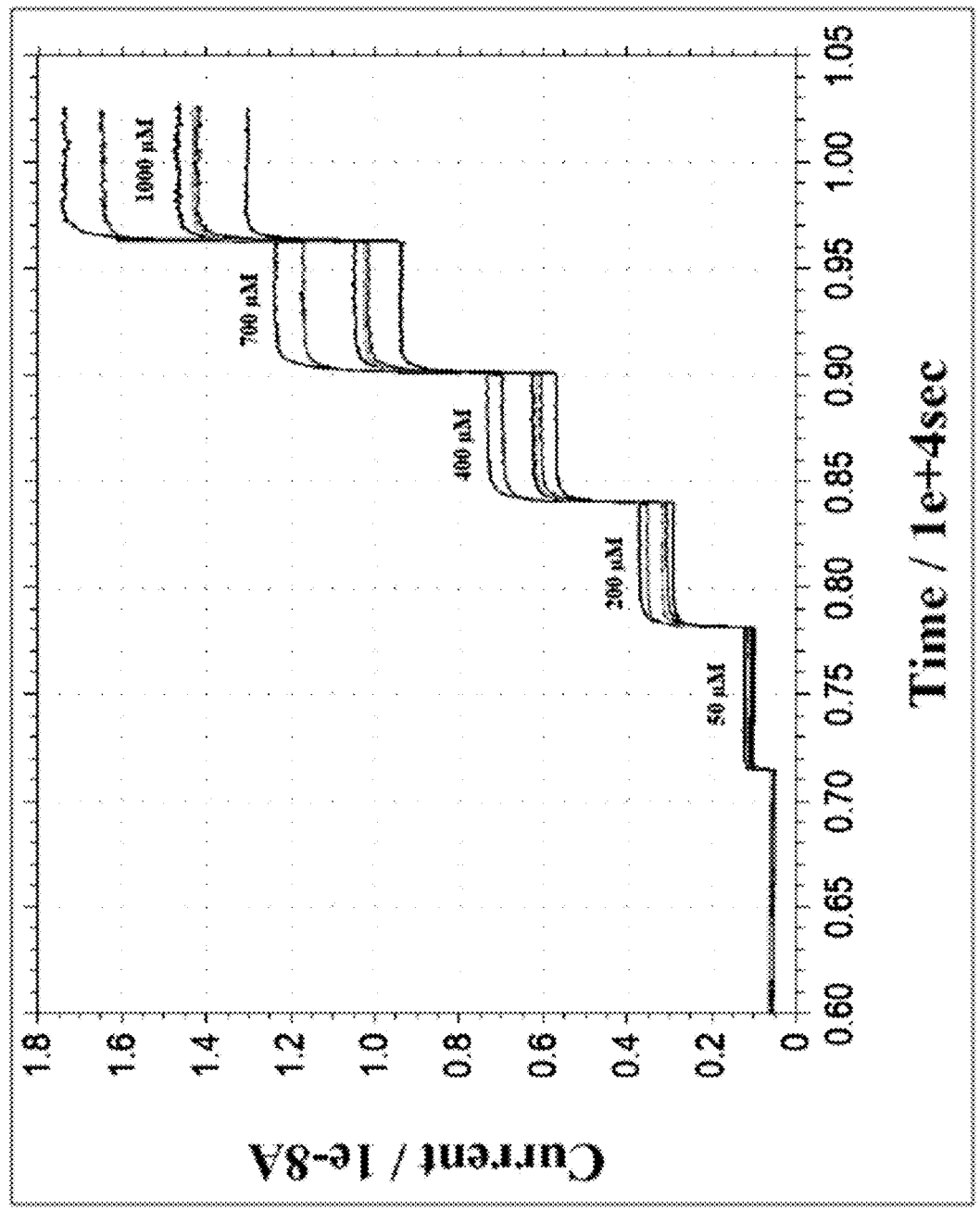
FIG. 1 is a graph of current produced by six example glucose sensors at glucose concentrations of 50 µM, 200 µM, 400 µM, 700 µM and 1,000 µM in phosphate buffered saline (PBS).

The following detailed description describes various features and functions of the disclosed systems and methods with reference to the accompanying figures. In the figures, similar symbols typically identify similar components, unless context dictates otherwise. The illustrative method and system embodiments described herein are not meant to be limiting. It will be readily understood that certain aspects of the disclosed methods and systems can be arranged and combined in a wide variety of different configurations, all of which are contemplated herein.

In one aspect, an analyte sensor is disclosed. The analyte sensor includes: a sensing membrane, wherein the sensing membrane can include:

a crosslinked network including one or more proteins and crosslinks, wherein the proteins are crosslinked through carbon-nitrogen double bonds between amine group nitrogen atoms on the proteins and carbon atoms in the crosslinks; and an analyte sensing component embedded in the crosslinked network.

In some embodiments, the analyte sensor is an enzyme-based biosensor. Biosensors can convert a signal produced by an analyte-concentration-dependent biochemical reaction into a measurable physical signal, such as an optical or electrical signal. Biosensors can be used in the detection of analytes in clinical, environmental, agricultural and biotechnological applications. Analytes that can be measured in clinical assays of fluids of the human body include, for example, glucose, lactate, cholesterol, bilirubin, proteins, lipids and electrolytes. The detection of analytes in biological fluids, such as blood, tear film, or intestinal fluid, can be important in the diagnosis and the monitoring of many diseases.

In some embodiments, the analyte sensor can be a component of a body-mountable device, such as an eye-mountable, tooth-mountable, or skin-mountable device. The eye-mountable device can be configured to monitor health-related information based on one or more analytes detected in a tear film (the term "tear film" is used herein interchangeably with "tears" and "tear fluid") of a user wearing the eye-mountable device. For example, the eye-mountable device can be in the form of a contact lens that includes a sensor configured to detect one or more analytes (e.g., glucose). The eye-mountable device can also be configured to monitor various other types of health-related information.

In some embodiments, the body-mountable device may comprise a tooth-mountable device. The tooth-mountable device may take the form of or be similar in form to the eye-mountable device, and be configured to detect at least one analyte in a fluid (e.g., saliva) of a user wearing the tooth-mountable device.

In some embodiments, the body-mountable device may comprise a skin-mountable device. The skin-mountable device may take the form of or be similar in form to the eye-mountable device, and be configured to detect at least one analyte in a fluid (e.g., perspiration, blood, etc.) of a user wearing the skin-mountable device.

The sensor as described herein can include one or more conductive electrodes through which current can flow. In some embodiments, the sensing membrane can be adjacent to a surface of an electrode. Depending on the application, the electrodes can be configured for different purposes. For example, a sensor can include a working electrode, a reference electrode, and a counter-electrode. Also possible are two-electrode systems, in which the reference electrode serves as a counter-electrode. The working electrode can be connected to the reference electrode via a circuit, such as a potentiostat.

The electrode can be formed from any type of conductive material and can be patterned by any process that be used for patterning such materials, such as deposition or photolithography, for example. The conductive materials can be, for example, gold, platinum, palladium, titanium, carbon, copper, silver/silver-chloride, conductors formed from noble materials, metals, or any combinations of these materials. Other materials can also be envisioned.

The sensing membrane can have a cross-linked network of one protein or a mixture of one or more different proteins. The proteins of the sensing membrane can be substantially unreactive in biochemical reactions, which will limit interference with the analyte sensing component. In some embodiments, the protein is bovine serum albumin.

The proteins can be about 15% by weight to about 50% by weight of the sensing membrane. In some embodiments, the proteins are about 15% by weight to about 20% by weight, about 20% by weight to about 25% by weight, about 25% by weight to about 30% by weight, about 30% by weight to about 35% by weight, about 35% by weight to about 40% by weight, about 40% by weight to about 45% by weight, or about 45% by weight to about 50% by weight of the membrane.

The proteins of the sensing membrane are covalently bound through crosslinks, forming a crosslinked network. The crosslinks can be between the one or more proteins in the sensing membrane, but can also be between the analyte sensing component, and/or one or more proteins and/or another analyte sensing component. In some embodiments, the crosslinks can be formed through carbon-nitrogen double bonds between the nitrogen atoms of amine groups on the proteins and/or analyte sensing component and carbon atoms in the crosslinks. These crosslinks can be derived from dialdehhyde compounds. For example, the crosslinks of the sensing membrane can have the structure of formula (I):

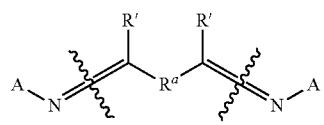

(I)

where A is independently a protein or an analyte sensing component, $R^a$ is $C_0$-$C_4$alkyl or a hydrophilic group, and R' is independently hydrogen or —$C_1$-$C_{12}$alkyl. The hydrophilic group can be soluble in water or a water-miscible solvent, such as an alcohol, and have one or more heteroatoms (e.g., nitrogen, oxygen or sulfur). In some embodiments, the crosslinks have one or more hydroxy groups. It is understood from formula (I) that the crosslinks have two carbons in addition to the $R^a$ group. Thus, crosslinks referred to herein as having a certain number of carbon atoms (e.g., $C_4$) will have an $R^a$ group with two less carbon atoms (e.g., $C_2$). For example, "$C_4$alkyl crosslinks" have an $R^a$ group that is $C_2$alkyl.

In some embodiments, the crosslinks can be formed through amide bonds between the nitrogen atoms of amine groups on the proteins and/or analyte sensing component and carbonyl groups in the crosslinks. These crosslinks can be derived from di-carbonyl compounds. For example, the crosslinks of the sensing membrane can have the structure of formula (Ia):

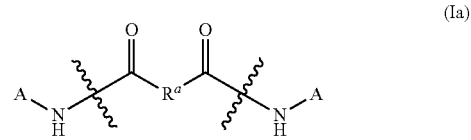

(Ia)

where A and $R^a$ are as described in formula (I).

In some embodiments, the crosslinks of the sensing membrane include one or more alkylene oxide units. The alkylene oxide units can be in the form of a polymer, such as poly(ethylene glycol), poly(propylene glycol), poly(butylene oxide) or a mixture thereof, and can be a copolymer including a combination of two or three different alkylene oxide units. In some embodiments, the poly(alkylene oxide) of the crosslinks is a block copolymer including blocks of two or three different poly(alkylene oxide) polymers. In certain embodiments, the poly(alkylene oxide) is a block copolymer of poly(ethylene glycol) and poly(propylene glycol). In other embodiments, the crosslinks and the second methacrylate-derived units include poly(ethylene glycol).

In some embodiments, the crosslinks of the sensing membrane include one or more ethylene oxide units. For example, the crosslinks (e.g., Ra in formula (I) above) can have the structure of formula (Ib):

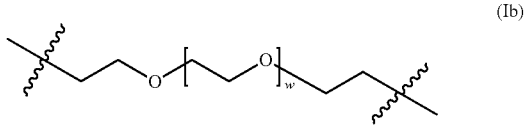

(Ib)

where w is 0, 1, 2, 3, 4, 5, 6, 7, 8, 9 or 10.

In certain embodiments, w is an average value of from about 2 to about 250.

In other embodiments, w in the crosslinks of formula (Ib) is such that the number average molecular weight ($M_n$) of the PEG portion (within the brackets in formula (Ib)) of the crosslinks is about 100 to about 10,000. For example, w can be selected such that the $M_n$ of the PEG portion of the crosslinks falls within a range in Table 1:

TABLE 1

$M_n$ range of the PEG portion of the crosslinks in the sensing membrane (values are approximate).

| Low | High |
|---|---|
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In some embodiments, the crosslinks of the sensing membrane are $C_2$-$C_6$alkyl. The crosslinks can be derived from oxaldehyde, malonaldehyde, succinaldehyde, glutaraldehyde or adipaldehyde.

The analyte sensing component is embedded, i.e., surrounded by the crosslinked network of sensing membrane. The embedded analyte sensing component is immobilized and can interact with a corresponding analyte of interest. In some embodiments, the analyte sensing component includes an enzyme.

The analyte sensing component of the analyte sensor can be selected to monitor physiological levels of a specific analyte. For example, glucose, lactate, cholesterol and various proteins and lipids can be found in body fluids, including, for example, tear film, and can be indicative of medical conditions that can benefit from continuous or semi-continuous monitoring.

The analyte sensing component can be an enzyme selected to monitor one or more analytes. For example, physiological cholesterol levels can be monitored with cholesterol oxidase, lactate levels with lactate oxidase, and glucose levels with glucose oxidase or glucose dehydrogenase (GDH).

In some embodiments, the analyte sensing component can be an enzyme that undergoes a chemical reaction with an analyte to produce detectable reaction products. For example, a copolymer including glucose oxidase ("GOx") can be situated around the working electrode to catalyze a reaction with glucose to produce hydrogen peroxide ($H_2O_2$). As shown below, the hydrogen peroxide can then be oxidized at the working electrode to release electrons to the working electrode, which generates a current.

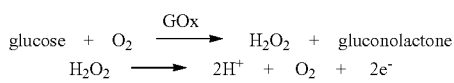

$$\text{glucose} + O_2 \xrightarrow{\text{GOx}} H_2O_2 + \text{gluconolactone}$$
$$H_2O_2 \longrightarrow 2H^+ + O_2 + 2e^-$$

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

In other embodiments, the analyte sensing component is glucose dehydrogenase (GDH). In certain instances, the use of GDH can include the addition of a cofactor such as flavin adenine dinucleotide (FAD), nicotinamide adenine dinucleotide (NAD), flavin mononucleotide, pyrroloquinoline quinone (PQQ) or a coenzyme.

The analyte sensing component can be present in about 40% to about 80% by weight in the sensing membrane. Is some embodiments, the analyte sensing component is present in the sensing membrane in about 40% by weight to about 50% by weight, about 50% by weight to about 60% by weight, about 60% by weight to about 70% by weight, or about 70% by weight to about 80% by weight.

The thickness of the sensing membrane can be from less than about 1 μm to about 10 μm. In some instances, the sensing membrane is less than about 2 μm in thickness, where in other applications the copolymer is about 2 μm to about 3 μm in thickness. In certain applications, the copolymer is about 2 μm to about 5 μm in thickness, where in other applications the copolymer is about 1 μm to about 3 μm or about 4 μm to about 5 μm in thickness. In some embodiments, the copolymer is about 1 μm to about 5 μm in thickness.

In another aspect, the analyte sensor can further include a protective membrane adjacent to a surface of the sensing membrane. The protective membrane has backbone chains that include:

first methacrylate-derived units, each having a hydrophilic side chain;

second methacrylate-derived units, each having a hydrophilic side chain;

third methacrylate-derived units; and hydrophilic crosslinks between the third methacrylate-derived units in different backbone chains.

Each of the first and second methacrylate-derived units of the backbones can be independently covalently bound to hydrophilic side chains. Each of the third methacrylate-derived units is covalently bound through a linker to another third methacrylate-derived unit in a different backbone chain. The hydrophilic crosslinks, or groups through which the third methacrylate-derived units are connected, are discussed in greater detail below. Various conformations and compositions of the hydrophilic side chains of the first and second methacrylate-derived units, and the hydrophilic crosslinks of the third methacrylate-derived units can be used to adjust the properties of the crosslinked, hydrophilic copolymer, which include, but are not limited to, hydrophilicity and permeability.

The hydrophilic side chains of the first and second methacrylate-derived units can be hydrophilic, and can be water soluble or soluble in a water-miscible solvent, such as an alcohol. The side chains can have one or more heteroatoms, for example, nitrogen, oxygen or sulfur atoms. In some embodiments, the side chains have one or more hydroxy groups. In some embodiments, the side chains of the first and second methacrylate-derived units can be the same or substantially the same. In other embodiments, they are different.

In some embodiments, the hydrophilic side chains of the first and second methacrylate-derived units include one or more alkylene oxide units. The alkylene oxide units can be in the form of a polymer, such as poly(ethylene glycol), polypropylene glycol), poly(butylene oxide) or a mixture thereof, and can be a copolymer including a combination of two or three different alkylene oxide units. In some embodiments, the poly(alkylene oxide) of the side chains is a block copolymer including blocks of two or three different poly(alkylene oxide) polymers. In certain embodiments, the poly(alkylene oxide) is block copolymer of poly(ethylene glycol) and poly(propylene glycol). In other embodiments, the hydrophilic side chain of the second methacrylate-derived unit, and the crosslinks both include poly(ethylene glycol).

In some embodiments, the first methacrylate-derived units of the protective membrane can have the structure of formula (II):

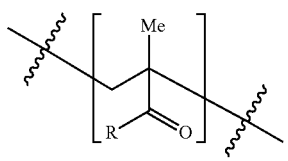
(II)

where R is a hydrophilic group. In certain embodiments, the hydrophilic group includes one or more hydroxy groups, such as an alcohol.

In some embodiments, the first methacrylate-derived units can have the structure of formula (IIa):

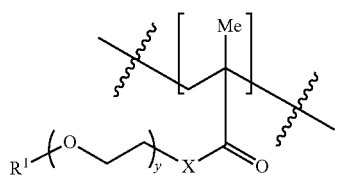
(IIa)

where X is —O—, —NR"— or —S—, y is 0, 1, 2, 3, 4, 5, 6, 7, 8, 9 or 10, and $R^1$ is hydrogen, —$C_1$-$C_{12}$alkyl, —$C_1$-$C_{12}$alkyl-OH, —SiR"$_3$, —C(O)—$C_1$-$C_{12}$alkyl, —$C_1$-$C_{12}$alkyl-C(O)OR", where R" is hydrogen or —$C_1$-$C_{12}$alkyl.

In certain embodiments, the first methacrylate-derived units have the structure:

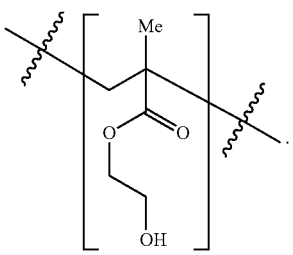

In some embodiments, the second methacrylate-derived units of the protective membrane can have the structure of formula (III):

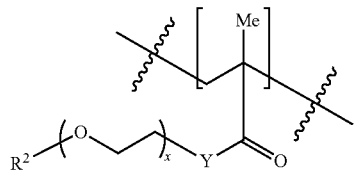
(III)

where Y is —O—, —NR"— or —S—, x is 1, 2, 3, 4, 5, 6, 7, 8, 9 or 10, and $R^2$ is hydrogen, —$C_1$-$C_{12}$alkyl, —SiR"$_3$, —C(O)—$C_1$-$C_{12}$alkyl, —$C_1$-$C_{12}$alkyl-C(O)OR", where R" is hydrogen or —$C_1$-$C_{12}$alkyl.

In certain embodiments, the second methacrylate-derived units can have the structure of formula (III) where x is an average value of from about 2 to about 250.

In some embodiments, the second methacrylate-derived units can have the structure of formula (III) where x is such that the poly(ethylene glycol) has a number average molecular weight ($M_n$) of about 100 to about 10,000. In certain embodiments, x is selected so that the $M_n$ of the poly(ethylene glycol) falls within a range in Table 2.

TABLE 2

$M_n$ range of poly(ethylene glycol) in the second methacrylate-derived units (values are approximate).

| Low | High |
|---|---|
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In certain embodiments, the second methacrylate-derived units can have the structure of formula (III), where Y is —O—, $R^2$ is methyl and x is such that the poly(ethylene glycol) has a number average molecular weight ($M_n$) of about 500.

In some embodiments, the presence of the second methacrylate-derived units having hydrophilic side chains in the crosslinked, hydrophilic copolymer of the analyte sensor can form a porous network. The structure of the porous network includes regions within the copolymer that are not occupied by polymer, these regions are referred to herein as "pores". The porous network of the crosslinked, hydrophilic copolymer can facilitate control of the equilibrium between the concentration of the analyte (e.g., glucose) in the sample solution, and the analyte concentration in the proximity of the analyte sensor electrode surface. When all of the analyte arriving at the analyte sensor is consumed, the measured output signal can be linearly proportional to the flow of the analyte and thus to the concentration of the analyte. However, when the analyte consumption is limited by the kinetics of chemical or electrochemical activities in the analyte sensor, the measured output signal may no longer be controlled by the flow of analyte and is no longer linearly proportional to the flow or concentration of the analyte. In this case, only a fraction of the analyte arriving at the analyte sensing component is consumed before the sensor becomes saturated, whereupon the measured signal stops increasing, or increases only slightly, with an increasing concentration of the analyte. The porous network can reduce the flow of the analyte to the analyte sensing component so the sensor does not become saturated and can therefore effectively enable a wider range of analyte concentrations to be measured.

The hydrophilic properties of the hydrophilic side chain of the second methacrylate-derived units can be varied to produce desired properties of the porous network, such as permeability of the analyte. For example, flow of the analyte into or across the sensor can be dependent on the specific analyte being monitored, and thus, the porous network can be altered to obtain properties for monitoring a specific analyte. In some applications, the hydrophilicity of the porous network can be adjusted by changing the number of alkylene oxide units in the hydrophilic side chain of the second methacrylate-derived units. Similarly, the hydrophilicity of the porous network can be adjusted by modifying the ratio of carbon atoms (i.e., —C—, —CH—, —CH$_2$— or —CH$_3$) to alkylene oxide units in the second methacrylate-derived units.

The crosslinks of the crosslinked, hydrophilic copolymer of the protective membrane connect the third methacrylate-derived units in different backbone chains, and are represented by $R^b$ in formula (IV):

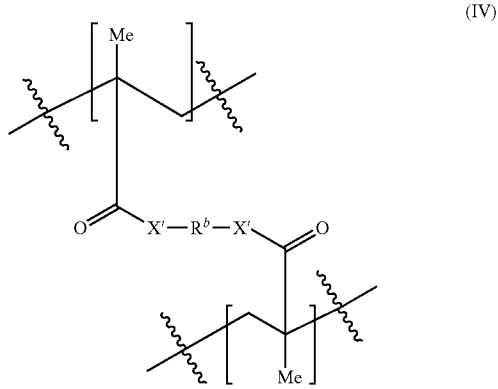

(IV)

where X' is independently —O—, —NR"— or —S—, and $R^b$ is a crosslink, where R" is hydrogen or —C$_1$-C$_{12}$alkyl.

In some embodiments, the crosslinks of the protective membrane can be soluble in water or a water-miscible solvent, such as an alcohol. The crosslinks can have one or more heteroatoms, for example, nitrogen, oxygen or sulfur atoms. In some embodiments, the crosslinks have one or more hydroxy groups.

In some embodiments, the crosslinks of the protective membrane can include one or more alkylene oxide units. The alkylene oxide units can be in the form of a polymer, such as poly(ethylene glycol), poly(propylene glycol), poly(butylene oxide) or a mixture thereof, and can be a copolymer including a combination of two or three different alkylene oxide units. In some embodiments, the poly(alkylene oxide) of the crosslinks is a block copolymer including blocks of two or three different poly(alkylene oxide) polymers. In certain embodiments, the poly(alkylene oxide) is a block copolymer of poly(ethylene glycol) and poly(propylene glycol). In other embodiments, the crosslinks include poly(ethylene glycol).

In some embodiments, the crosslinks of the protective membrane include one or more ethylene oxide units. For example, the crosslinks (e.g., $R^b$ in formula IV above) can have the structure of formula (IVa):

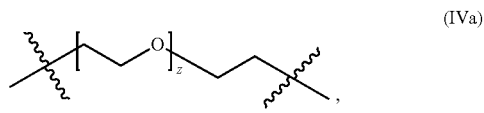

(IVa)

where z is 0, 1, 2, 3, 4, 5, 6, 7, 8, 9 or 10. In certain embodiments, the crosslinks of the protective membrane have the structure of formula (IVa) where z is an average value of from about 2 to about 250.

In other embodiments, z in the crosslinks of formula (IVa) is such that the number average molecular weight ($M_n$) of the PEG portion (within the brackets in formula (IVa)) of the crosslinks is about 100 to about 10,000. For example, z can be selected such that the $M_n$ of the PEG portion of the crosslinks falls within a range in Table 3:

TABLE 3

$M_n$ range of the PEG portion of the crosslinks in the protective membrane (values are approximate).

| Low | High |
|---|---|
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In some embodiments, the crosslinks of the protective membrane are derived from di(ethylene glycol) dimethacrylate, i.e., crosslinks of formula (IV) where X' is —O—, and $R^b$ is —CH$_2$CH$_2$OCH$_2$CH$_2$—, or of formula (IVa) where z is 1.

In some embodiments, the crosslinked copolymer of the protective membrane can form a porous network. The structure of the porous network includes regions or voids within the copolymer that are not occupied by copolymer, and are referred to herein as "pores". The porous network of the crosslinked copolymer can facilitate control of the equilibrium between the concentration of the analyte (e.g., glucose) in the sample, and the analyte concentration in the proximity of the analyte sensor electrode surface. When all of the analyte arriving at the analyte sensor is consumed, the measured output signal can be linearly proportional to the flow of the analyte and thus to the concentration of the analyte. However, when the analyte consumption is limited by the kinetics of chemical or electrochemical activities in the analyte sensor, the measured output signal may no longer be controlled by the flow of analyte and may no longer be linearly proportional to the flow or concentration of the analyte. In this case, only a fraction of the analyte arriving at the analyte sensing component is consumed before the sensor becomes saturated, whereupon the measured signal stops increasing, or increases only slightly, with an increasing concentration of the analyte. The porous network can reduce the flow of the analyte to the analyte sensing component so the sensor does not become saturated and can therefore enable a wider range of analyte concentrations to be measured.

The properties of the porous network can be varied to produce desired properties, such as permeability of the analyte. For example, flow of the analyte into sensing membrane can be dependent on the specific analyte being monitored, and thus, the porous network can be altered to obtain properties for monitoring a specific analyte. Variation of the second methacrylate-derived units can increase or decrease the permeability of the protective membrane.

The thickness of the crosslinked, hydrophilic copolymer of the protective membrane can vary depending on the desired properties of the analyte sensor. The thickness of the copolymer, as measured from the outward facing surface of sensing membrane to the outward facing surface of the copolymer, can play an important role in regulating the flow of the analyte to the analyte sensing component. Depending on the characteristics of the methacrylate-derived units in the copolymer the type of analyte sensing component used, and the analyte to be monitored, the thickness of the copolymer can be from less than about 10 μm to about 30 μm. In some instances, the copolymer is less than 20 μm in thickness, where in other applications the copolymer is about 20 μm to about 25 μm in thickness. In certain applications, the copolymer is about 10 μm to about 15 μm in thickness, where in other applications the copolymer is about 15 lam to about 20 μm or about 25 μm to about 30 μm in thickness. In some embodiments, the copolymer is about 20 μm in thickness.

In some embodiments, the sensing membrane can completely or substantially cover one or more surfaces of the electrode to which it is adjacent. In analyte sensors lacking a crosslinked, hydrophilic copolymer, the sensing membrane can completely or substantially cover one or more surfaces of the electrode, so as to create a barrier or membrane between the electrode and, when present, an analyte sample being monitored or measured. In such embodiments, the sensing membrane is between the electrode and the analyte sample. The sensing membrane can completely cover the electrode to limit the direct contact of the electrode with the sample.

In analyte sensors having a crosslinked, hydrophilic copolymer, the sensing membrane can act as a barrier or membrane between the electrode and the crosslinked, hydrophilic copolymer. The sensing membrane can completely or substantially cover one or more surfaces of the electrode to which it is adjacent. The copolymer can be adjacent to, and completely or substantially cover, the sensing membrane, so as to create a barrier or membrane between the sensing membrane and, when present, the analyte sample being monitored or measured. In such embodiments, the sensing membrane is between the electrode and the copolymer, and the copolymer is between the sensing membrane and the analyte sample. The sensing membrane can completely cover the electrode to limit the direct contact of the electrode with the copolymer and/or the analyte sample, and the copolymer can completely cover the sensing membrane to limit the direct contact of the analyte sample with the sensing membrane without first passing through the copolymer.

In some embodiments, the electrode can have an inward facing surface and an outward facing surface, with the outward facing surface completely or substantially covered by a sensing membrane. The sensing membrane can also have an inward facing surface and an outward facing surface. The outward facing surface of the electrode can be adjacent to and/or in contact with the inward facing surface of the sensing membrane, and the outward facing surface of the sensing membrane can be adjacent to and/or in contact with, when present, the analyte sample being monitored or measured.

When the analyte sensor comprises a crosslinked, hydrophilic copolymer, the electrode can have an inward facing surface and an outward facing surface, with the outward facing surface completely or substantially covered by a sensing membrane. The sensing membrane can also have an inward facing surface and an outward facing surface. The outward facing surface of the electrode can be adjacent to and/or in contact with the inward facing surface of the sensing membrane, and the outward facing surface of the sensing membrane can be completely or substantially covered by a crosslinked, hydrophilic copolymer. The copolymer can have an inward facing surface and an outward facing surface. The inward facing surface of the copolymer can be adjacent to and/or in contact with the outward facing surface of the sensing membrane, and the outward facing surface of the copolymer can be adjacent to/or in contact with, when present, the analyte sample being monitored or measured.

As used herein, a material that can "completely cover" or a surface that is "completely covered" refers to greater than about 95% coverage. In some embodiments, this can refer to greater than about 99% coverage. As used herein, a material that can "substantially cover" or a surface that is "substantially covered" refers to greater than about 75% coverage. In some embodiments, this can refer to great than about 85% coverage, up to about 95% coverage.

In another aspect, methods for making an analyte sensor are disclosed. The method can involve the formation of a sensing membrane, which includes:

a) forming a sensing mixture including one or more proteins, a crosslinking agent, and an analyte sensing component, wherein the proteins have one or more amine functional groups;

b) depositing the sensing mixture onto a surface of an electrode; and c) curing the deposited sensing mixture to provide a sensing membrane.

In some embodiments of the method for forming the sensing membrane, the mixture is formed by combining three separate solutions. The method can involve:

a) forming a first mixture which includes one or more proteins having one or more amine functional groups;

b) forming a second mixture which includes a crosslinking agent;

c) forming a third mixture which includes an analyte sensing component;

d) combining the three mixtures to provide the sensing mixture.

In some embodiments, the sensing membrane can be formed on a surface of an electrode. For example, each component, or a combination of one or more components, can be individually deposited on a surface of an electrode to form the deposited sensing mixture. Similarly, when the mixture is formed by combining three separate solutions, the solutions can be combined on a surface of an electrode to form the sensing mixture.

The proteins of the sensing mixture can be selected to provide the proteins of the sensing membrane as discussed herein. In some embodiments, the proteins of the sensing mixture are all the same, or substantially the same protein. Two or more proteins can also be used to form the crosslinked sensing membrane. In some embodiments, the proteins are bovine serum albumin.

The crosslinking agent of the sensing mixture is a chemically reactive species that is capable of forming covalent bonds between the proteins of the sensing membrane, and/or covalent bonds between the analyte sensing component and one or more proteins and/or another analyte sensing component in the sensing membrane. In some embodiments, the crosslinking agent can form carbon-nitrogen double bonds between the nitrogen atoms of amine groups on the proteins and/or analyte sensing component and carbon atoms in the crosslinking agent. In some embodiments, the crosslinking agent can be a di-carbonyl compound. For example, the crosslinking agent can have the structure of formula (V):

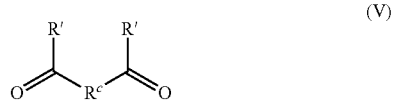

(V)

where $R^c$ and $R'$ are selected to provide the crosslinks of the sensing membrane described herein. In some embodiments, $R^c$ is $C_0$-$C_4$alkyl or a hydrophilic group, and $R'$ is independently hydrogen, chloro, —$C_1$-$C_{12}$alkyl or N-hydroxysuccinimide. In some embodiments, the crosslinking agent can be oxaldehyde, malonaldehyde, succinaldehyde, glutaraldehyde or adipaldehyde. In other embodiments, the hydrophilic group can be selected to provide the crosslinks of the sensing membrane described herein.

The analyte sensing component can be selected based on the analyte desired to be monitored. For example, to monitor physiological cholesterol levels, cholesterol oxidase can be used, and to monitor lactate levels lactate oxidase can be used. To monitor glucose levels, the analyte sensing component can include glucose oxidase or glucose dehydrogenase (GDH).

The analyte sensing component can be present when the proteins in the deposited sensing membrane mixture are crosslinked, such that crosslinking results in the formation of a crosslinked network in which the analyte sensing component is embedded. The embedded analyte sensing component is immobilized and can be used to monitor a corresponding analyte of interest.

In some embodiments, the method further includes the formation of a protective membrane, which includes:

a) forming a copolymer mixture including an initiator, a first methacrylate monomer having a hydrophilic side chain, a dimethacrylate monomer, and a second methacrylate monomer having a hydrophilic side chain;

b) depositing the copolymer mixture onto a surface of the sensing membrane; and c) subjecting the deposited copolymer mixture to conditions sufficient to initiate polymerization (i.e., curing).

In some embodiments of the method, the copolymer mixture is formed by combining separate solutions of the copolymer precursors. The method can involve:

a) forming a first mixture which includes a dimethacrylate monomer, an initiator, and first methacrylate monomer having a hydrophilic side chain;

b) forming a second mixture which includes a dimethacrylate monomer, an initiator, and second methacrylate monomer having a hydrophilic side chain; and d) combining the mixtures to provide the copolymer mixture.

In some embodiments of the method for forming the protective membrane, the initiator and/or the dimethacrylate monomer can be present in any of the mixtures. For example, the first or second mixture can include an initiator and/or a dimethacrylate monomer. In other embodiments of the method for forming the protective membrane, the third mixture is not present and the dimethacrylate monomer is present in the first and/or second mixture.

The first and second methacrylate monomers of the copolymer mixture include hydrophilic side chains that can have one or more heteroatoms. The hydrophilic side chains can include one or more alkylene oxide units to form the crosslinked, hydrophilic copolymer of the analyte sensor as described herein.

The first methacrylate monomer of the copolymer mixture can be selected to provide the first methacrylate-derived units of the crosslinked, hydrophilic copolymer as described herein. In some embodiments of the method, the first methacrylate monomer has the structure of formula (VI):

(VI)

where R is a hydrophilic group. In certain embodiments of the method, the hydrophilic group includes one or more hydroxy groups, such as an alcohol.

In some embodiments of the method, the first methacrylate monomer has the structure of formula (VIa):

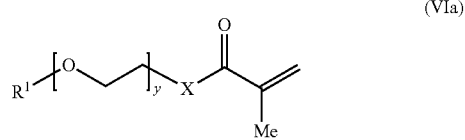

(VIa)

where X, y, $R^1$, and R" are selected to provide the first methacrylate-derived monomeric unit of the crosslinked, hydrophilic copolymer described herein.

In certain embodiments of the method, the first methacrylate monomer has the structure:

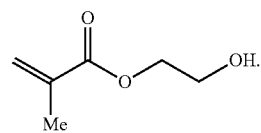

The second methacrylate monomer of the copolymer mixture can be selected to provide the second methacrylate-derived units of the crosslinked, hydrophilic copolymer as described herein. In some embodiments of the method, the second methacrylate monomer has the structure of formula (VII):

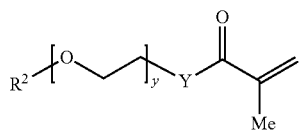

(VII)

where Y, x, $R^2$ and R" are selected to provide the second methacrylate-derived monomeric unit of the crosslinked, hydrophilic copolymer described herein.

In some embodiments of the method, the second methacrylate monomer has the structure of formula (VII) where x is selected to provide second methacrylate-derived monomeric units of the crosslinked, hydrophilic copolymer described herein where the poly(ethylene glycol) has a number average molecular weight ($M_n$) of about 100 to about 10,000. In certain embodiments, x is selected to provide second methacrylate-derived monomeric units where the $M_n$ of the poly(ethylene glycol) falls within a range in Table 2.

In certain embodiments of the method, the second methacrylate monomer has the structure of formula (VII), where Y is —O—, $R^2$ is methyl and x is such that the poly(ethylene glycol) has a number average molecular weight ($M_n$) of about 500.

The dimethacrylate monomer of the copolymer mixture is a molecule having two terminal methacrylate groups tethered by a hydrophilic linker. The hydrophilic linker is selected to provide the crosslinks between third methacrylate-derived units in different backbone chains of the crosslinked, hydrophilic copolymer described herein. In embodiments where the mixture is formed from the combination of two or more solutions each having a dimethacrylate monomer, the dimethacrylate monomers can be the same, or in some instances, can be different.

The extent of crosslinking in crosslinked, hydrophilic copolymer of the protective membrane can be controlled by adjusting the amount of dimethacrylate monomer in the mixture. In some embodiments, the dimethacrylate monomer can be about 1% to about 15% of the mixture. In other examples, the amount is about 1% to about 5%, or about 5% to about 10%, or about 10% to about 15%. In some embodiments, the amount is about 1%. In some instances, both the first and second mixtures include about 1% of the dimethacrylate monomer.

The dimethacrylate monomer of the copolymer mixture can be selected to provide the crosslinks of the crosslinked, hydrophilic copolymer as described herein. In some embodiments of the method, the dimethacrylate monomer includes one or more alkylene oxide units to provide the crosslinks of the crosslinked, hydrophilic copolymer as described herein. In some embodiments, the dimethacrylate monomer includes poly(ethylene glycol) (PEG). For example, the dimethacrylate monomer can have the structure of formula (VIII):

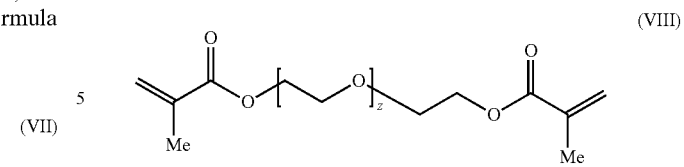

(VIII)

where z is 0, 1, 2, 3, 4, 5, 6, 7, 8, 9 or 10.

In certain embodiments of the method, the dimethacrylate monomer can have the structure of formula (VIII) where z is an average value of from about 2 to about 250.

In other embodiments of the method, the dimethacrylate monomer can have the structure of formula (VIII) where z is such that the number average molecular weight ($M_n$) of the PEG portion of the dimethacrylate monomer is about 100 to about 10,000. For example, w can be selected such that the $M_n$ of the PEG portion of the dimethacrylate monomer falls within a range in Table 3. In some embodiments, the dimethacrylate monomer is di(ethylene glycol) dimethacrylate.

The sensing and copolymer mixtures of the method can be formed in an aqueous medium, alcoholic medium, or mixture thereof. The aqueous medium can include a buffered aqueous solution, such as, for example, a solution containing citric acid, acetic acid, borate, carbonate, bicarbonate, 4-2-hydroxyethyl-1-piperazineethanesulfonic acid (HEPES), 3-{[tris(hydroxymethyl)methyl]amino-}-propanesulfonic acid (TAPS), N,N-bis(2-hydroxyethyl)glycine (Bicine), tris(hydroxymethyl)methylamine (Tris), N-tris(hydroxymethyl)methylglycine (Tricine), 3-[N-Tris(hydroxymethyl)methylamino]-2-hydroxypropanesulfonic acid (TAPSO), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), saline sodium citrate (SSC), 2-(N-morpholino)ethanesulfonic acid (MES), 2(R)-2-(methylamino)succinic acid, or phosphate buffered saline (PBS). In some embodiments, the mixture can be formed in a mixture of a buffered aqueous solution and ethanol.

In some embodiments of the method, the mixtures and solutions of the method can be formed with approximately the same concentration of component (e.g., protein, analyte sensing component, first methacrylate monomer, etc.). The percentage of each component can then be varied by adjusting the amounts of each individual mixture used to form the mixture used for forming the sensing or protective membranes. In some instances, the percentage of analyte sensing component in the sensing membrane mixture, can be about 40% by weight to about 80% by weight, the proteins can be about 15% by weight to about 50%, and the crosslinking agent can be about 1% by weight to about 10% by weight. In certain examples, the percentage of analyte sensing component in the sensing membrane mixture, can be about 60% by weight to about 70% by weight, the proteins can be about 25% by weight to about 35% by weight, and the crosslinking agent can be about 1% by weight to about 5% by weight. In the protective membrane mixture, the percentage of first methacrylate monomer can be about 20% by weight to about 60% by weight, the percentage of second methacrylate monomer can be about 10% by weight to about 40% by weight, and the percentage of dimethacrylate monomer can be about 0.1% by weight to about 5% by weight. All percentages are given as a percentage of the cumulative amount of analyte sensing component, first methacrylate monomer and second methacrylate monomer. In certain examples, the percentage of analyte sensing component is about 40% by weight, the amount of first methacrylate monomer is about 35% by weight to about 40% by weight, and the amount of second methacrylate monomer is about 20% by weight to about 25% by weight. In certain embodiments of the method, the mixture can be thoroughly mixed, optionally with a stirrer or shaker, before being deposited.

The ratio of the components in each mixture can vary depending on the desired properties of the resulting analyte sensor. For example, adjusting the amount of the second methacrylate monomer having a hydrophilic side chain can alter the porous network of the protective membrane. Controlling the properties of the porous network can allow for the tuning of the permeability of the analyte sensor. Similar tunability can also be accomplished by adjusting the amount of the sensing mixture deposited on the electrode, and/or adjusting the amount of the second methacrylate monomer combined with the first methacrylate monomer.

Depositing the sensing mixture onto a surface of an electrode, or the copolymer mixture onto a surface of the sensing membrane can be accomplished by a number of methods. For example, the depositing can be performed manually with a micro-syringe, or by automated fabrication processes with nano jet dispensing equipment.

In some embodiments of the methods, the amount of the sensing or copolymer mixture deposited is selected to provide the desired thickness of the sensing or protective membrane of the analyte sensor, respectively. In some embodiments, the amount deposited on the electrode is about 50 nL/mm$^2$ to about 500 nL/mm$^2$. In other examples, the amount is about 50 µm to about 150 µm, or about 150 µm to about 300 µm, or about 300 µm to about 500 µm in thickness. In some embodiments, the amount is about 100 nL/mm$^2$. In some instances, depositing about 100 nL/mm$^2$ of the sensing or copolymer mixture provides a sensing membrane or protective membrane, respectively, that is about 20 µm in thickness.

Conditions suitable to initiate polymerization (i.e., curing) can be selected based on the characteristics of the components being polymerized, and as so not to degrade the analyte sensing component. In embodiments where the analyte sensing component is an enzyme, the temperature and pH of the method can be selected to preserve the activity of the enzyme. In certain embodiments the initiator is activated with ultraviolet (UV) light. For example, when 2,2-diemthoxy-2-phenylacetophenone is used as an initiator, curing can be performed with UV light. In other instances, curing is performed by air-drying at ambient or elevated temperature. In embodiments where the mixture is formed from the combination of two or more solutions each having an initiator, the initiators can be the same, or in some instances, can be different.

Although the crosslinked, hydrophilic copolymers in the above examples comprise methacrylate groups, there are a number of ethylenically unsaturated groups known in the art to be capable of undergoing polymerization. Ethylenically unsaturated monomers and macromers may be either acrylic- or vinyl-containing. Vinyl-containing monomers contain the vinyl grouping ($CH_2$=CH—), and are generally highly reactive. Acrylic-containing monomers are represented by the formula:

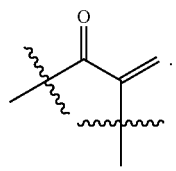 [SMILES: *C(=C)C(*)=O]

Examples of suitable polymerizable groups may include acrylic-, ethacrylic-, itaconic-, styryl-, acrylamido-, methacrylamido- and vinyl-containing groups such as the allyl group.

In addition to the above disclosed methods of forming crosslinked, hydrophilic copolymers by the polymerization of ethylenically unsaturated monomers and macromonomers, additional chemistries will be known to one or ordinary skill in the art to from such copolymers. As an example, epoxy chemistry, in which multifunctional amines and multifunctional epoxy compounds are mixed together and cured, can be used to form crosslinked, hydrophilic copolymers. Additionally, urethane chemistry may be used, in which multifunctional isocyanates are mixed with multifunctional alcohols and cured to provide crosslinked, hydrophilic copolymers. Other chemistries for the formation of crosslinked, hydrophilic copolymers exist, and will be well known to those of ordinary skill in the art.

It should be understood that arrangements described herein are for purposes of example only. As such, those skilled in the art will appreciate that other arrangements and other elements (e.g., machines, interfaces, functions, orders, and groupings of functions, etc.) can be used instead, and some elements can be omitted altogether according to the desired results. Further, many of the elements that are described are functional entities that can be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used.

Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

EXAMPLES

Example 1

Formation of a Two-Layer Analyte Sensor

Formation of the sensing membrane:
A solution of glucose oxidase (10.0 mg) and BSA (Albumin from bovine serum, 4.0 mg) in 200 uL PBS buffer was formed. To this mixture was added 12.0 uL glutaraldehyde (50% solution in water), and the resulting mixture was mixed. The mixture was deposited (120 mL) onto a sensor area of 1×3 mm, and air dried overnight at ambient temperature and pressure.
Formation of the protective membrane:
Two solutions (A and B) were prepared:
A) 2-hydroxyethyl methacrylate monomer solution containing 1% by weight di(ethylene glycol) dimethacrylate and 1% by weight 2,2-dimethoxy-2-phenylacetophenone.
B) poly(ethylene glycol) methyl ether methacrylate (average Mn 500, Aldrich product #447943) monomer solution containing 1% by weight di(ethylene glycol) dimethacrylate and 1% by weight 2,2-dimethoxy-2-phenylacetophenone.
The two solutions were combined with PBS buffer in a ratio of 0.225:0.175:0.200 A:B:PBS and thoroughly mixed with a vortex shaker. The resulting mixture was deposited (100 nL/mm$^2$) onto a surface of the sensing membrane, and the deposited mixture was UV-cured for 5 minutes at 365 nm under nitrogen with an EC-500 light exposure chamber (Electro-Lite Corp). The resulting cured crosslinked, copolymer protective membrane had a thickness of about 20 μm.

Example 2

Analyte Sensor Performance in a Glucose Solution

Figure 2:
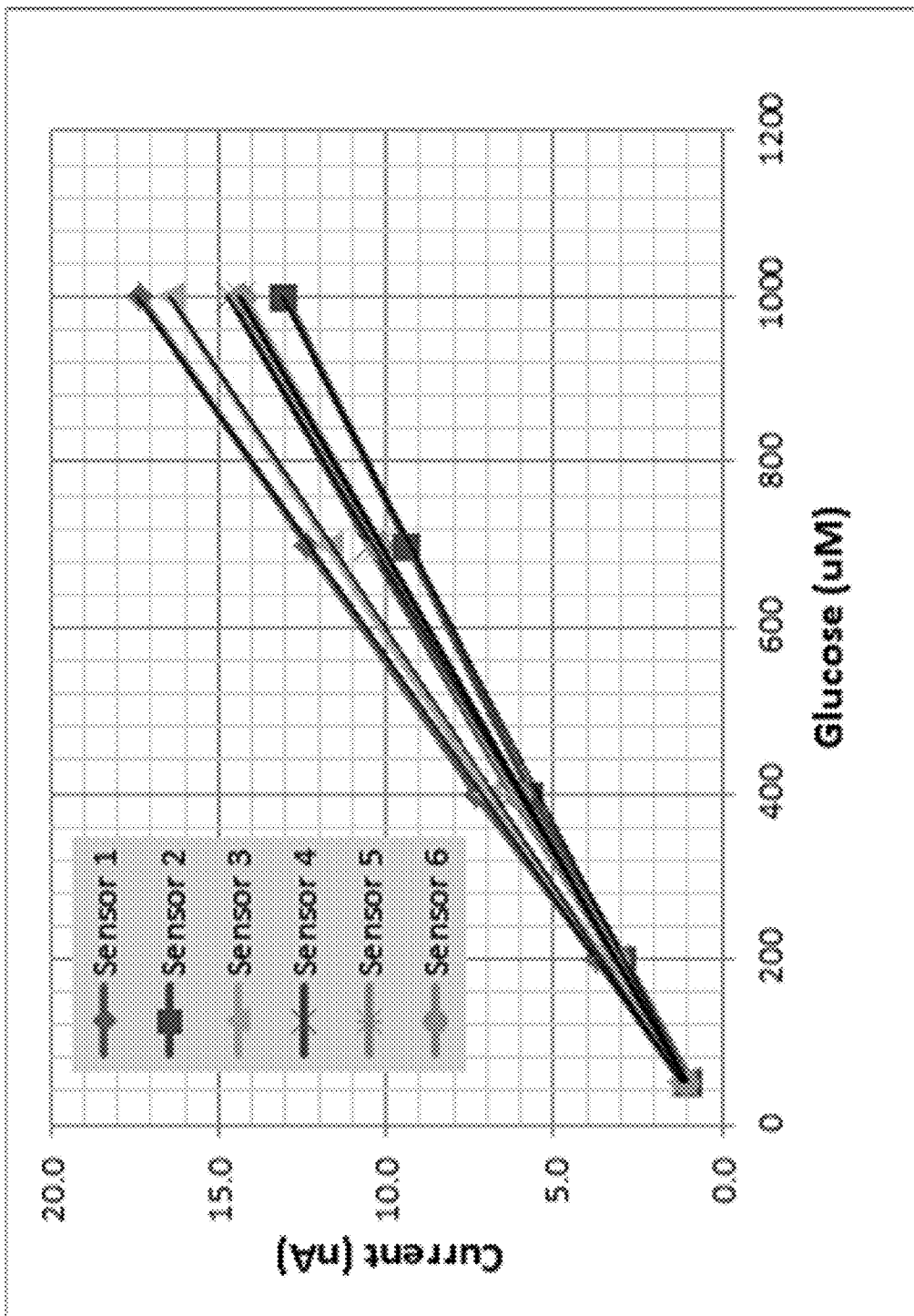
FIG. 2 is a graph of the relationship between current and glucose concentration observed in the six example glucose sensors of FIG. 1 at glucose concentrations of 50 µM, 200 µM, 400 µM, 700 µM and 1,000 µM in phosphate buffered saline (PBS).
Figure 3:
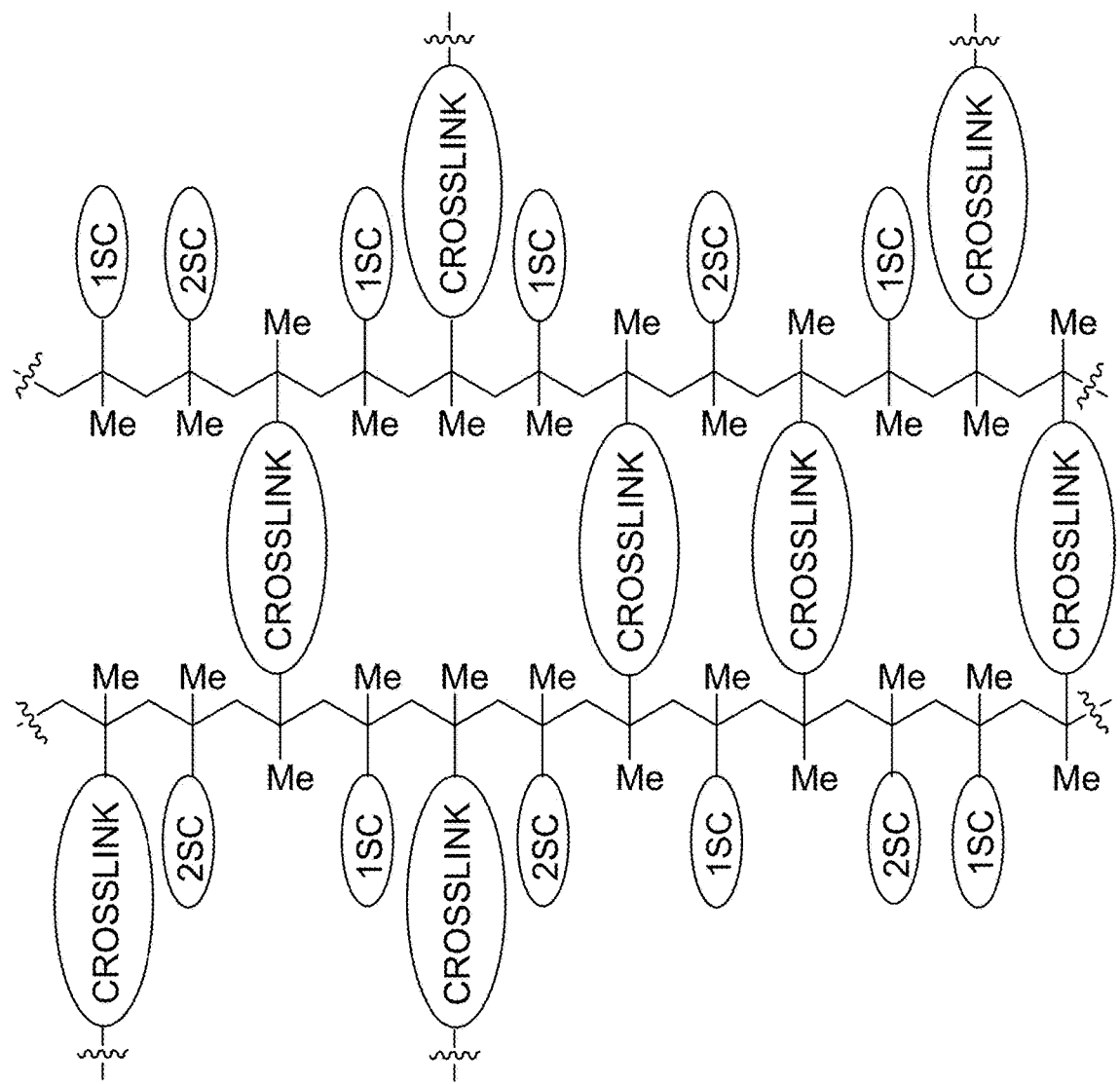
FIG. 3 is a representative diagram of a crosslinked, hydrophilic copolymer, in accordance with an example embodiment. The diagram shows a two-backbone section of the copolymer, and each 1SC ("first side chain") represents a hydrophilic side chain connected to a first methacrylate-derived unit, and each 2SC ("second side chain") represents a hydrophilic side chain connected to a second methacrylate-derived unit. Each CROSSLINK represents a hydrophilic crosslink between third methacrylate-derived units in different backbone chains.

Six analyte sensors made according to Example 1 were tested at concentrations of glucose in phosphate buffered saline (PBS) ranging from 50 μM to 1000 μm. The sensors were submerged in PBS and the glucose concentration was increased every 10-15 minutes. The current generated at the electrode of each sensor was measured using a potentiostat (FIG. 1). A linear relationship between current and glucose concentration was observed (FIG. 2).

The invention claimed is:
1. An analyte sensor comprising:
a sensing membrane comprising:
a crosslinked network comprising one or more proteins and crosslinks, wherein
the proteins are crosslinked through carbon-nitrogen double bonds between amine group nitrogen atoms on the proteins and carbon atoms on the crosslinks; and
an analyte sensing component embedded in the crosslinked network;
a protective membrane adjacent to a surface of the sensing membrane, comprising
backbone chains comprising:
first methacrylate-derived units, each having a hydrophilic side chain;
second methacrylate-derived units, each having a hydrophilic side chain comprising one or more alkylene oxide unit; and
third methacrylate-derived units; and
hydrophilic crosslinks between the third methacrylate-derived units in different backbone chains, wherein the hydrophilic crosslinks comprise poly(alkylene oxide).

2. The analyte sensor of claim 1, wherein in the crosslinks of the sensing membrane are $C_2$-$C_6$alkyl.

3. The analyte sensor of claim 1, wherein the crosslinks of the sensing membrane comprise one or more alkylene oxide unit.

4. The analyte sensor of claim 1, wherein the proteins of the sensing membrane are bovine serum albumin.

5. The analyte sensor of claim 1, wherein the analyte sensing component of the sensing membrane comprises glucose oxidase.

6. The analyte sensor of claim 1, wherein the sensing membrane is adjacent to a surface of an electrode.

7. The analyte sensor of claim 6, wherein the sensing membrane is between the electrode and the protective membrane.

8. The analyte sensor of claim 1, wherein the first methacrylate-derived units of the protective membrane have the structure of formula (IIa):

(IIa)

wherein
X is —O—, —NR"— or —S—;
y is 0-10; and
$R^1$ is hydrogen, —$C_1$-$C_{12}$alkyl, —$C_1$-$C_{12}$alkyl-OH, —SiR"$_3$, —C(O)—$C_1$-$C_{12}$alkyl, —$C_1$-$C_{12}$alkyl-C(O)OR", wherein R" is —$C_1$-$C_{12}$alkyl.

9. The analyte sensor of claim 8, wherein the first methacrylate-derived units of the protective membrane have the structure:

10. The analyte sensor of claim 1, wherein the second methacrylate-derived units of the protective membrane have the structure of formula (III):

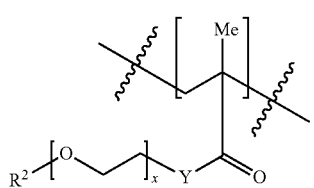
(III)

wherein
Y is —O—, —NR"— or —S—;
R² is hydrogen, —C₁-C₁₂alkyl, —SiR"₃, —C(O)—C₁-C₁₂alkyl, —C₁-C₁₂alkyl-C(O)OR",
where R" is hydrogen or —C₁-C₁₂alkyl; and
x is 1-10.

11. The analyte sensor of claim 1, wherein the second methacrylate-derived units of the protective membrane have the structure of formula: (III):

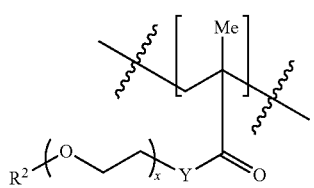
(III)

wherein
Y is —O—, —NR"— or —S—;
R² is hydrogen, —C₁-C₁₂alkyl, —SiR"₃, —C(O)—C₁-C₁₂alkyl, —C₁-C₁₂alkyl-C(O)OR",
where R" is hydrogen or —C₁-C₁₂alkyl; and
x is an average value of from 2 to about 250.

12. The analyte sensor of claim 1, wherein the protective membrane has a thickness of about 20 µm.

13. The analyte sensor of claim 1, wherein
the proteins of the sensing membrane are BSA;
the crosslinks of the sensing membrane are C₂-C₆alkyl;
the analyte sensing component of the sensing membrane comprises glucose oxidase.

14. The analyte sensor of claim 1, wherein
the first methacrylate-derived units of the protective membrane are derived from 2-hydroxyethylmethacrylate;
the second methacrylate-derived units of the protective membrane have the structure of formula (III):

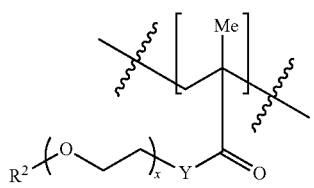
(III)

wherein
Y is —O—, —NR"— or —S—;
R² is hydrogen, —C₁-C₁₂alkyl, —SiR"₃, —(O)—C₁-C₁₂alkyl-C(O)OR", where R" is hydrogen or —C₁-C₁₂alkyl; and
x is an average value of from about 10 to about 15; and
the hydrophilic crosslinks of the protective membrane have the structure of formula (IVa):

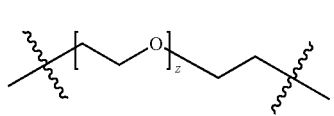
(IVa)

wherein z is 2-10.

15. The analyte sensor of claim 1, wherein
the proteins of the sensing membrane are BSA;
the crosslinks of the sensing membrane are C₅alkyl;
the analyte sensing component of the sensing membrane comprises glucose oxidase;
the first methacrylate-derived units of the protective membrane are derived from 2-hydroxyethylmethacrylate;
the second methacrylate-derived units of the protective membrane have the structure of formula (III):

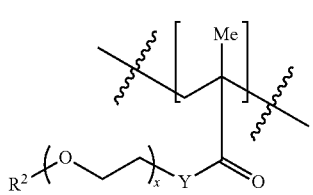
(III)

wherein x is an average value of from about 10 to about 15; and
the hydrophilic crosslinks of the protective membrane have the structure of formula (IVa):

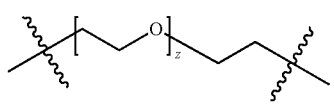
(IVa)

wherein z is 2-10.

16. The analyte sensor of claim 1, wherein the hydrophilic crosslinks of the protective membrane have the structure of formula (IVa):

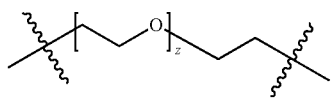
(IVa)

wherein z is an average value of from about 2 to about 250.

17. The analyte sensor of claim 1, wherein
the first methacrylate-derived units of the protective membrane are derived from 2-hydroxyethylmethacrylate;
the second methacrylate-derived units of the protective membrane have the structure of formula (III):

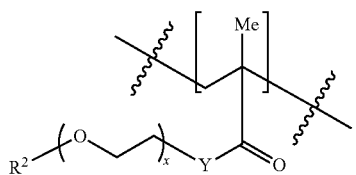

(III)

wherein

Y is —O—, —NR"— or —S—;

R² is hydrogen, —C₁-C₁₂alkyl, —SiR"₃, —C(O)—C₁-C₁₂alkyl, —C₁-C₁₂alkyl-C(O)OR", where R" is hydrogen or —C₁-C₁₂alkyl; and x is an average value of from about 10 to about 15; and the hydrophilic crosslinks of the protective membrane have the structure of formula (IVa):

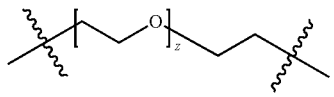

(IVa)

wherein z is an average value of from about 2 to about 250.

18. A method for manufacturing an analyte sensor, the method comprising:

forming a sensing mixture comprising one or more proteins, a crosslinking agent, and an analyte sensing component, wherein the proteins have one or more amine functional groups;

depositing the sensing mixture onto a surface of an electrode;

curing the deposited sensing mixture to provide a sensing membrane;

forming a copolymer mixture comprising an initiator, a first methacrylate monomer having a hydrophilic side chain comprising one or more alkylene oxide unit, a dimethacrylate monomer, and a second methacrylate monomer having a hydrophilic side chain, wherein the dimethacrylate monomer comprises two terminal methacrylate groups tethered by a hydrophilic linker comprising poly(alkylene oxide);

depositing the copolymer mixture onto a surface of the sensing membrane; and curing the deposited copolymer mixture to provide a protective membrane.

* * * * *